United States Patent
Schjøtt et al.

(10) Patent No.: US 11,703,182 B2
(45) Date of Patent: Jul. 18, 2023

(54) METHOD AND SYSTEM OF LUBRICATING CONSUMERS TO BE MONITORED VIA THEIR LUBRICANT

(71) Applicant: Vestas Wind Systems A/S, Aarhus N. (DK)

(72) Inventors: Simon Schjøtt, Åbyhøj (DK); Thomas Korsgaard Nielsen, Vejle (DK); Jan Hove Pedersen, Risskov (DK); Sascha Gutt, Højbjerg (DK); Daniel Henriksen, Aarhus C (DK)

(73) Assignee: Vestas Wind Systems A/S, Aarhus N (DK)

( * ) Notice: Subject to any disclaimer, the term of this patent is extended or adjusted under 35 U.S.C. 154(b) by 167 days.

(21) Appl. No.: 17/126,486

(22) Filed: Dec. 18, 2020

(65) Prior Publication Data

US 2021/0207768 A1 Jul. 8, 2021

Related U.S. Application Data

(63) Continuation of application No. 14/419,146, filed as application No. PCT/DK2012/050300 on Aug. 16, 2012, now abandoned.

(Continued)

(51) Int. Cl.
*F16N 29/00* (2006.01)
*F16N 25/00* (2006.01)
(Continued)

(52) U.S. Cl.
CPC ............ *F16N 29/04* (2013.01); *F03D 80/70* (2016.05); *F16N 25/00* (2013.01); *F16N 29/00* (2013.01);

(Continued)

(58) Field of Classification Search
CPC . F16N 7/40; F16N 13/22; F16N 25/00; F16N 29/00; F16N 2200/04; G01N 33/2858
See application file for complete search history.

(56) References Cited

U.S. PATENT DOCUMENTS 5,610,341 A 3/1997 Tortora
5,696,331 A 12/1997 Otsuka et al.
(Continued)

FOREIGN PATENT DOCUMENTS

CN 201547476 U 8/2010
CN 102084128 A 6/2011
(Continued)

OTHER PUBLICATIONS

International Searching Authority, International Search Report and Written Opinion issued in corresponding Application No. PCT/DK2012/050300, dated Dec. 18, 2013, 8 pages.

(Continued)

*Primary Examiner* — Minh Truong
(74) *Attorney, Agent, or Firm* — Wood Herron & Evans LLP

(57) ABSTRACT

A method involves directing lubricant to different consumers which are to be monitored via their lubricant. The lubricant is drained through drain lines connected to the consumers and directed to a tank. At least some the lubricant in the drain lines or the consumers is extracted into extraction lines. Flow from the extraction lines is selectively directed to a measurement device, which then measures a characteristic of the lubricant. A system for carrying out such a method is also provided, wherein the system includes a multiplexer for selectively directing flow from the extraction lines.

9 Claims, 4 Drawing Sheets

Related U.S. Application Data

(60) Provisional application No. 61/678,111, filed on Aug. 1, 2012.

(51) Int. Cl.
   *F16N 39/06* (2006.01)
   *F16N 29/04* (2006.01)
   *G01N 33/28* (2006.01)
   *F03D 80/70* (2016.01)

(52) U.S. Cl.
   CPC ......... *F16N 39/06* (2013.01); *G01N 33/2858* (2013.01); *F16N 2200/04* (2013.01); *F16N 2210/025* (2013.01); *Y02E 10/72* (2013.01)

(56) References Cited

U.S. PATENT DOCUMENTS

| | | | |
|---|---|---|---|
| 5,754,055 | A | 5/1998 | McAdoo et al. |
| 6,105,724 | A | 8/2000 | Stitz et al. |
| 7,163,086 | B2 | 1/2007 | Care et al. |
| 7,886,875 | B2 | 2/2011 | Shevchencko et al. |
| 8,190,394 | B2 | 5/2012 | Davis et al. |
| 8,869,940 | B2 | 10/2014 | Johnson et al. |
| 2002/0195296 | A1 | 12/2002 | Maret et al. |
| 2008/0150518 | A1 | 6/2008 | Becker et al. |
| 2009/0014245 | A1 | 1/2009 | Shevchenko et al. |
| 2012/0025526 | A1 | 2/2012 | Luo et al. |
| 2012/0025529 | A1 | 2/2012 | Davis et al. |
| 2012/0168254 | A1* | 7/2012 | Matousek ................. F16N 7/40 184/6.12 |
| 2013/0332045 | A1 | 12/2013 | Uluyol et al. |
| 2015/0343346 | A1 | 12/2015 | Sheridan |

FOREIGN PATENT DOCUMENTS

| | | |
|---|---|---|
| CN | 201941100 U | 8/2011 |
| CN | 102345723 A | 2/2012 |
| DE | 3931497 A1 | 4/1991 |
| EP | 0408758 A1 | 1/1991 |
| EP | 0715118 A1 | 6/1996 |
| EP | 2169221 A2 | 3/2010 |
| JP | S5954896 A | 3/1984 |
| JP | H04262193 A | 9/1992 |
| WO | 0032980 A1 | 6/2000 |
| WO | 03029671 A1 | 4/2003 |
| WO | 2004113689 A2 | 12/2004 |
| WO | 2007088015 A1 | 8/2007 |
| WO | 2009147147 A3 | 1/2010 |

OTHER PUBLICATIONS

European Patent Office, Opposition in EP 12750705.1, dated Aug. 25, 2017.
A1, Merkmalsgliederung des Anspruchs 1.
A2, Merkmalsgliederung des Anspruchs 8.
Intellectual Property India, Examination Report in Indian Application No. 683/DELNP/2015, dated Jun. 20, 2019.
The State Intellectual Property Office of China, First Notification of Office Action in CN Application No. 201280075025.7, dated Nov. 23, 2015.
The State Intellectual Property Office of China, 2nd Notification of Office Action in CN Application No. 201280075025.7, dated Jul. 13, 2016.
The State Intellectual Property Office of China, 3rd Notification of Office Action in CN Application No. 201280075025.7, dated Mar. 13, 2017.

* cited by examiner

METHOD AND SYSTEM OF LUBRICATING CONSUMERS TO BE MONITORED VIA THEIR LUBRICANT

CROSS REFERENCE TO RELATED APPLICATIONS

This application is a continuation of U.S. patent application Ser. No. 14/419,146, filed Jun. 1, 2015 (pending), which is a U.S. National Phase Application of International Application No. PCT/DK2012/050300, filed Aug. 16, 2012 (expired), which claimed the benefit of U.S. Provisional Application Ser. No. 61/678,111, filed Aug. 1, 2012 (expired), the disclosures of which are incorporated by reference herein in their entirety.

TECHNICAL FIELD

The present invention relates to lubrication systems and methods where consumers are monitored via their lubricant. The systems and methods are especially relevant to wind turbines.

BACKGROUND

A wind turbine (also referred to as a "wind turbine generator" or WM) includes many moving parts that facilitate converting the kinetic energy of the wind into electrical energy. This is particularly evident in the power transmission system of a wind turbine, which often includes one or more main bearings, a gearbox, and a generator for processing rotational mechanical energy from a rotor of the wind turbine. The components of the power transmission system typically require some form of lubrication to help reduce friction and wear. Thus, wind turbines typically include one or more lubrication systems for these and other components.

It is advantageous to monitor the condition of lubricant in a lubrication system for a variety of reasons. For example, the presence of large particles (greater than approximately 70 μm) in lubricant drained from a component often means the component has become worn or damaged beyond acceptable levels. Lubrication systems sometimes include particle counters to detect the presence and quantity of such particles so that appropriate action can be taken to minimize further wear or damage.

Typically a particle counter or other measurement device is placed in the drain lines of each component whose condition is being monitored via the lubricant. This increases the cost and complexity of the lubrication system.

SUMMARY

The present invention provides a method of lubrication that allows the health or other aspects of multiple consumers to be monitored via their lubricant. The term "consumer" refers to a component having one or more rotating parts to be lubricated. According to the method, lubricant is directed to different consumers whose lubricant is to be analyzed. The lubricant is later drained through drain lines connected to the consumers and directed to a tank. At least some the lubricant in the drain lines or the consumers is extracted into extraction lines. The method further involves selectively directing flow from the extraction lines to a measurement device. As used herein, the term "selectively directing" refers to selecting an output from multiple inputs and changing the selection based on observed activity and/or predetermined time periods; the output may correspond to one of the inputs or a subset of the inputs.

The measurement device to which lubricant is directed measures a property of the lubricant. The property may be any characteristic of the lubricant, such as pressure, temperature, viscosity, oxidation, water content, flow rate, etc. In one particular embodiment, the measurement device is a particle counter such that measuring a characteristic of the lubricant comprises counting particles in the lubricant. This may be for monitoring oil cleanliness or for detecting wear in one or more of the consumers beyond an acceptable level (health monitoring). Either way, the method may further involve collecting particles greater than a predetermined minimum size in a particle collector downstream from the particle counter.

A lubrication system for carrying out the above-mentioned method is also provided. The lubrication system includes the tank, the drain lines configured to receive lubricant from the different consumers, the extraction lines connected to the drain lines or the consumers, and the measurement device. A multiplexer connected to the extraction lines selectively directs flow to the output line. Thus, as used herein, the term "multiplexer" refers to the device or arrangement of components that selectively directs flow from the extraction lines to the output line. The measurement device connected to the output line is configured to measure a characteristic of the lubricant, as mentioned above.

DETAILED DESCRIPTION

Figure 1:
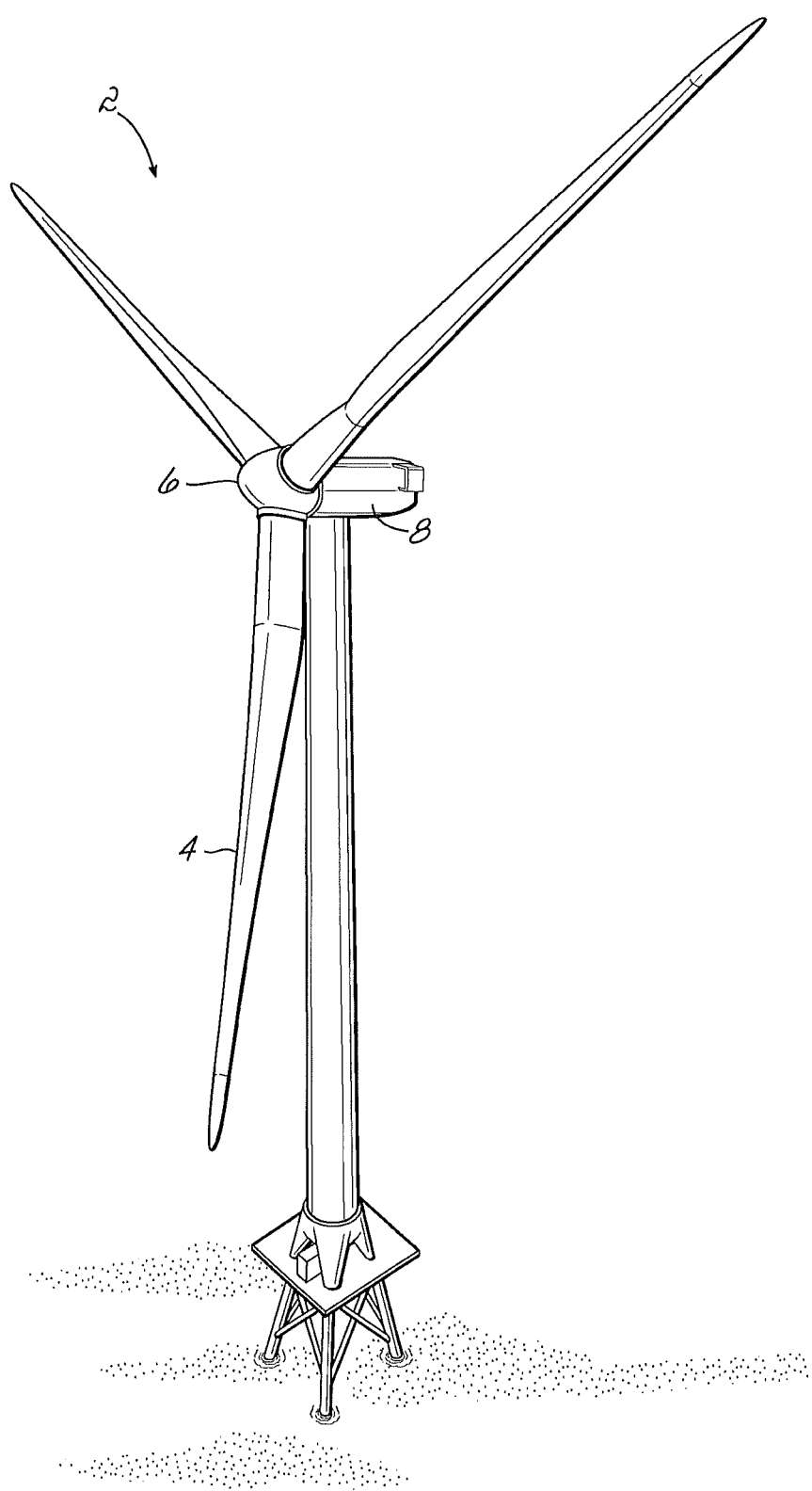
FIG. 1 is a perspective view of one example of a wind turbine.

FIG. 1 shows one example of a wind turbine 2. Although an offshore wind turbine is shown, it should be noted that the description below may be applicable to other types of wind turbines. Indeed, the description below relates to a system and method of lubrication that may be applicable to a wide range of industrial products or systems, including those in other industries. A wind turbine is shown and described simply to facilitate discussion.

Figure 2:
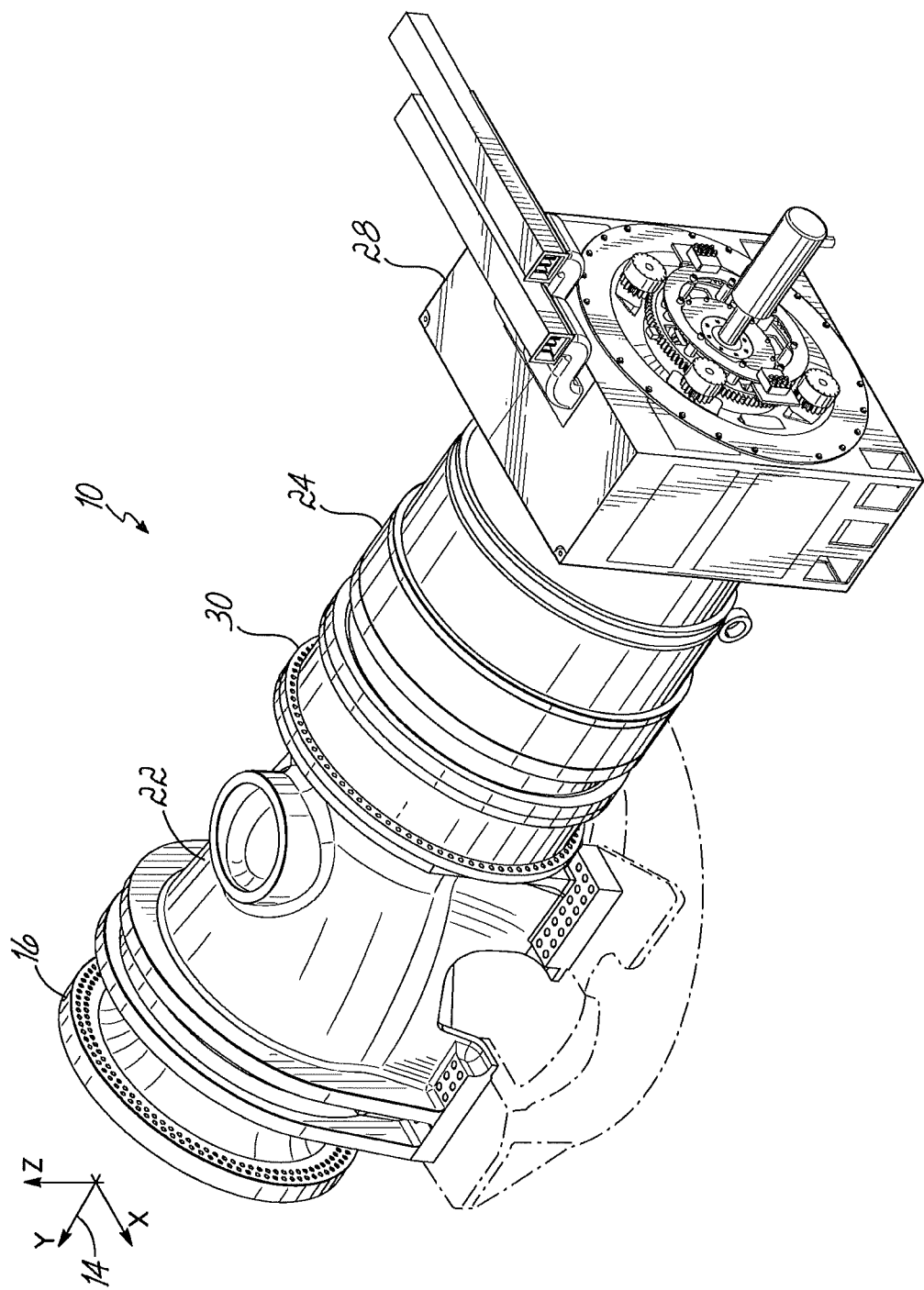
FIG. 2 is a perspective view of a power transmission system for the wind turbine of FIG. 1.

With this in mind, the wind turbine 2 includes rotor blades 4 mounted to a hub 6, which is supported by a nacelle 8 on a tower 12. Wind causes the rotor blades 4 and hub 6 to rotate about a main axis 14 (FIG. 2). This rotational energy is delivered to a power transmission system (or "power train") 10 housed within the nacelle 8. In the representative embodiment shown in FIGS. 2 and 3, the power transmission system 10 includes a main shaft 16 coupled to the hub 6 (FIG. 1). The power transmission system 10 also includes first and second main bearings 18, 20 supporting the main shaft 16, a bearing housing 22 surrounding the first and second main bearings 18, 20, and a gearbox 24 having a gearbox input member connected to the main shaft 16 by a coupling 30. The gearbox 24 increases the rotational speed of the main shaft 16 to drive a generator 28.

Figure 3:
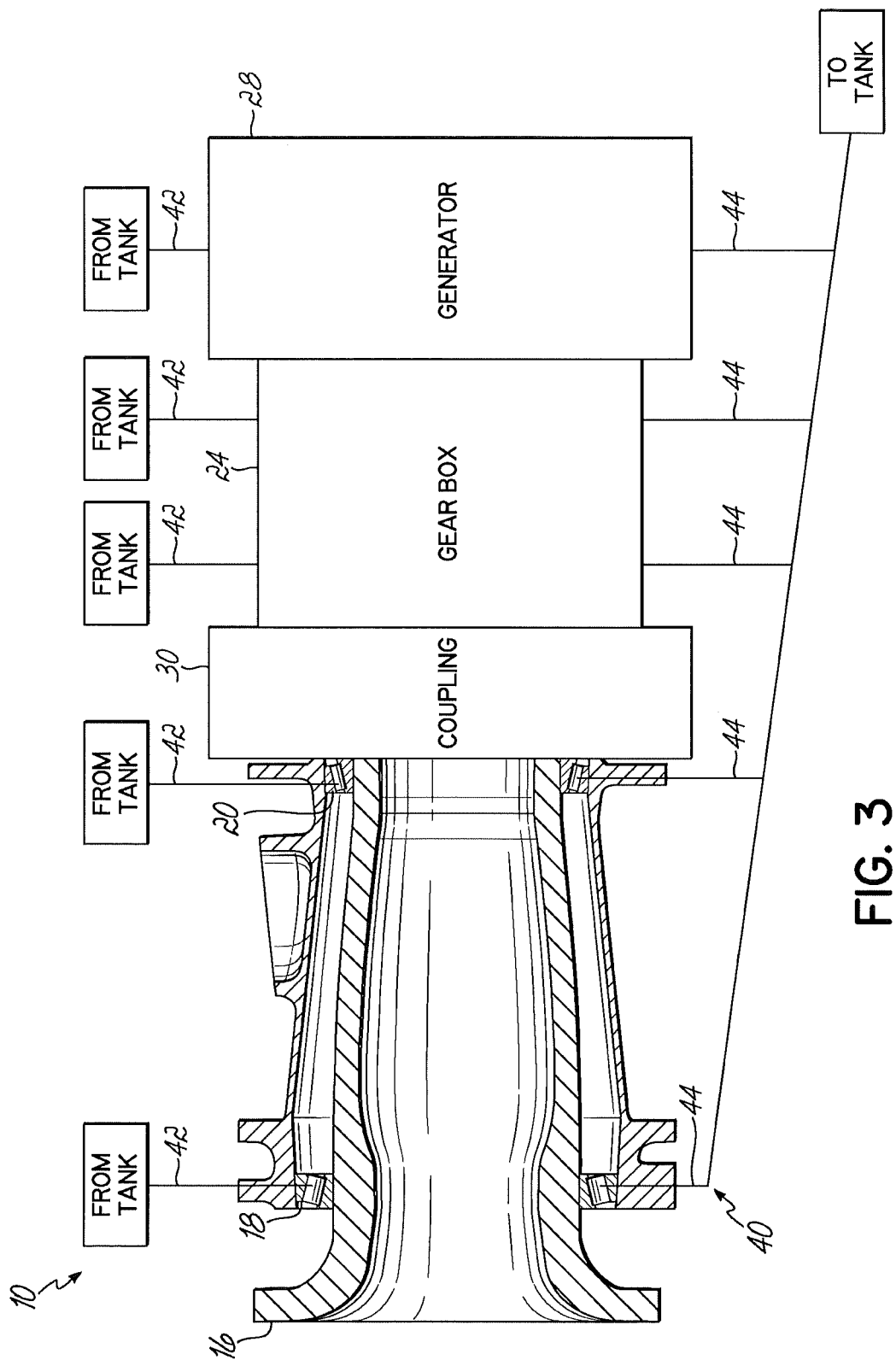
FIG. 3 is a cross-sectional view of the power transmission system of FIG. 2.

Other arrangements for the power transmission system 10 are possible. Accordingly, the components of the power transmission system 10 and their operation need not be described in further detail. Only aspects pertaining to their lubrication are described below. Indeed, as schematically shown in FIG. 3, the first and second main bearings 18, 20, gearbox 24, and generator 28 are "consumers" of lubricant in a lubrication system 40. Each contains moving parts to be lubricated and are supplied with lubricant from a tank (i.e., reservoir) via one or more feed lines 42. Drain lines 44 allow lubricant to return to the tank after passing through the consumers. There may be a single or multiple drain lines per consumer depending on the design of the lubrication system. The gearbox in the figures is an example of the latter (e.g., the drain lines 44 of the gearbox 24 may be associated with different gear stages). The coupling 30 is not shown as having a feed line or drain line, but could have such lines in alternative embodiments.

Figure 4:
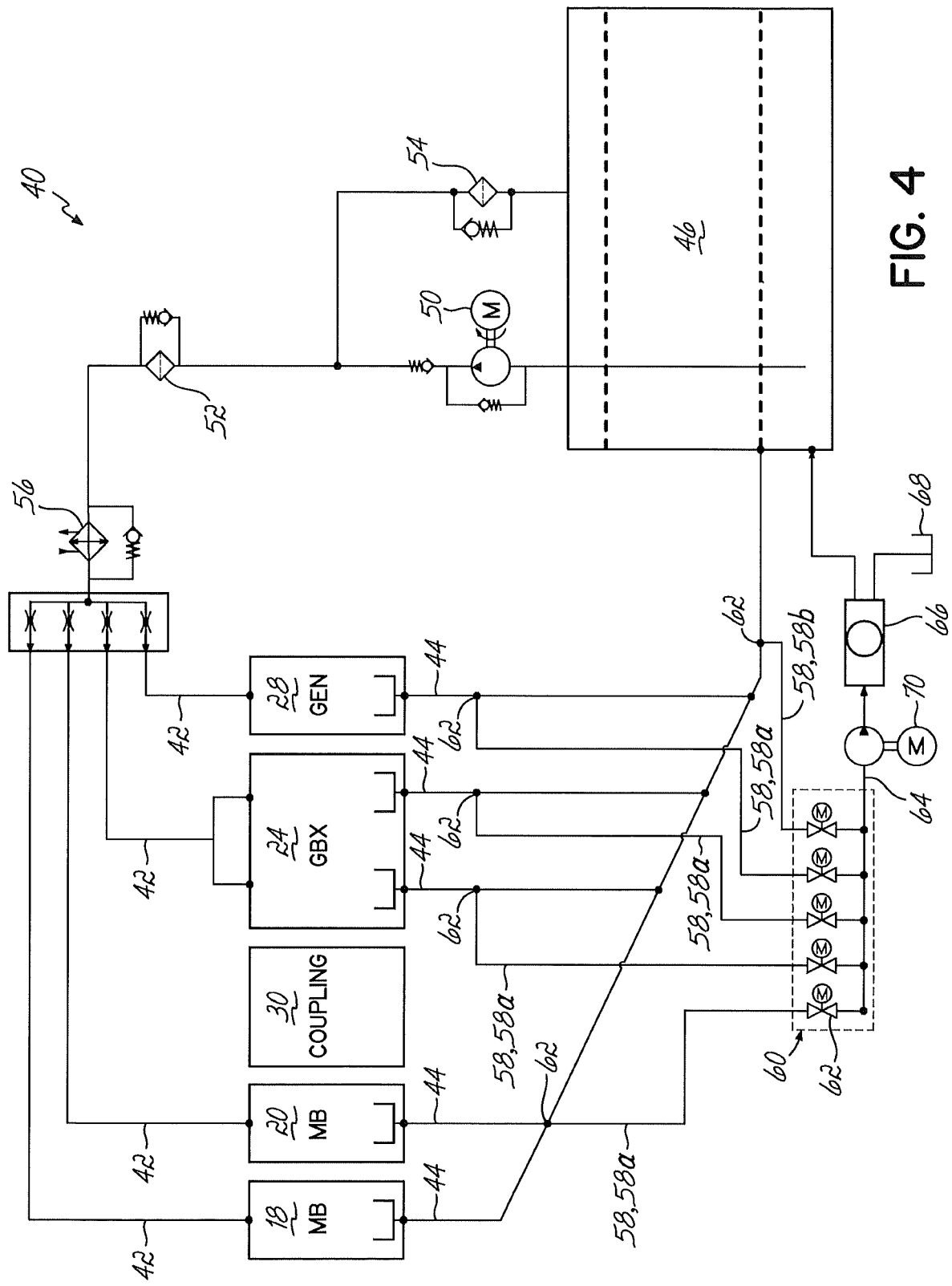
FIG. 4 is a schematic view of a lubrication system for the power transmission system of FIGS. 2 and 3.

FIG. 4 illustrates one possible embodiment of the lubrication system 40 in further detail. The lubrication system 40 includes a fluid circuit between tank 46 and feed lines 42. Because the fluid circuit may be arranged in ways other than what is shown, it will not be described in detail. Standard features/components, such as a pump 50 for delivering lubricant from the tank 46, an inline filtration system 52, an offline filtration system 54, and a heat exchanging system 56, may be provided.

The drain lines 44 connected to the consumers are eventually combined and run to the tank 46. Extraction lines 58 ("probe lines") are connected to the drain lines 44 before they converge. The extraction lines 58 direct at least some lubricant from the drain lines 44 to a multiplexer 60. Probe points 62 for the extraction lines 58 are located in the drain lines 44 so that extraction lines 58a are each associated with a respective consumer (note: an exception in the embodiment shown is a common extraction line 58a for the first and second main bearings 18, 20). A common extraction line 58b may also be provided downstream from where the drain lines 44 converge so as to be associated with a combined flow from the consumers.

The multiplexer 60 in FIG. 4 is an arrangement of valves 62 that are controlled to selectively direct flow from the extraction lines 58 to an output line 64. In other words, the multiplexer 60 selects which of the extraction lines 58 communicate with the output line 64. This selection is alternated between the extraction lines 58, as will be described below.

The lubrication system 40 further includes a measurement device 66 connected to the output line 64 downstream of the multiplexer 60. The measurement device 66 is configured to measure at least one characteristic of the lubricant in the output line 64. In the embodiment shown, the measurement device 66 is a particle counter configured to detect particles in the lubricant received from the multiplexer 60. The particle counter normally allows the lubricant to return to the tank 46, but directs particles greater than a predetermined minimum size to a particle collector 68. The predetermined minimum size may be 70 μm, for example. Particles of such size in wind turbine lubrication systems are often indicators of wear or damage in the consumer beyond an acceptable level. A pump 70 may be connected to the output line 64 of the multiplexer 60 to ensure lubricant is drawn from the extraction lines 58 to the measurement device 66. The multiplexer 60 may alternatively or additionally be arranged so that gravity ensures flow from the extraction lines 58.

In use, lubricant is directed to the different consumers 18, 20, 24, 28 via the feed lines 42. After passing through the consumers, the lubricant enters the drain lines 44 so as to be directed toward the tank 46. At least some the lubricant is extracted into the extraction lines 58. Under normal operating conditions the multiplexer 60 directs a combined flow from the consumers to the output line 64. This may be achieved by closing the valves 62 of the extraction lines 58a and opening the valve of the common extraction line 58b. In other embodiments not shown, the combine flow may be the result of all extraction lines 58a being open to the output line 64 such that the common extraction line 58b is not necessary. If the measurement device 66 detects particles greater than 70 μm, the multiplexer 60 selects one of the extraction lines 58a to direct to the output line 64 while blocking the remaining extraction lines 58. This selection is alternated if particles greater than 70 pm are not detected after a predetermined time interval. Thus, the multiplexer 60 switches between the individual extraction lines 58a to identify the source of the large particles so that appropriate action may be taken. The particles registered and counted by the particle counter (i.e., those exceeding 70 μm) are gathered by the particle collector 68. This may be achieved by physical entrapment, magnetic attraction, or other known methods.

As can be appreciated, on a broad level the lubrication system 40 provides the following functionalities: 1) measuring a characteristic (e.g., counting particles) of a combined flow of lubricant from all consumers, and 2) measuring a characteristic of the flow of lubricant from individual consumers. The first functionality may be achieved as described above, namely by connecting a common extraction line 58b to a point in the lubrication system 40 downstream from where the drain lines 44 converge, or by combining flow from various extraction lines 58a. The second functionality includes switching between the extraction lines to search for which consumer is the source of an observed characteristic, which is particularly advantageous when the lubrication system 40 is used to monitor health. The additional functionality of particle collection may be provided when the characteristic of the lubricant being measured is particle size.

It should be noted that the lubrication system 40 also offers advantages in terms of oil sampling capabilities. The ability to switch between the extraction lines 58 means that oil samples can be taken from the different consumers during different stages of the wind turbine's operation. For example, at a first time period after startup, the multiplexer 60 may switch between the extraction lines 58 so that lubricant from the different consumers can be analyzed by the measuring device 60 or otherwise. The sampling can then be repeated at a different time after startup to observe characteristics during a different stage of operation.

It should also be kept in mind that the embodiments described above are merely examples of the invention defined by the claims that appear below. Additional advantages, examples, and modifications will be appreciated. For example, the extraction lines 58 may be connected to the consumers themselves rather than to the drain lines 44. Moreover, the multiplexer 60 may be a different arrangement of valves or other mechanical components (e.g., actuators) capable of switching between different flow lines. Finally, although there are advantages to switching between combined and individual flows, lubrication systems and methods where there is only measurement of individual flows are possible.

With this in mind, the details of any particular embodiment should not be seen to necessarily limit the scope of the claims below. In addition to appreciating other modifications and variations, skilled persons will understand how features of various embodiments may be combined in different ways.

The invention claimed is:

1. A wind turbine power transmission system having different consumers of lubrication to be monitored via their lubricant, the power transmission system including a lubrication system, the lubrication system comprising:
 a tank;
 drain lines configured to receive lubricant from the different consumers, the drain lines being connected to the tank;
 extraction lines connected to the drain lines or the consumers;
 a multiplexer connected to the extraction lines, the multiplexer having an output line and being configured to selectively direct flow from the extraction lines to the output line;
 a measurement device connected to the output line, the measurement device being configured to measure a characteristic of the lubricant in the output line, wherein the measurement device includes a particle counter configured to detect particles in the lubricant received from the multiplexer and a particle collector connected to the particle counter and configured to remove particles greater than a predetermined minimum size detected by the particle counter from the lubricant; and
 a pump connected to the output line, the pump being configured to draw lubricant through the multiplexer.

2. The wind turbine power transmission system of claim 1, wherein the multiplexer comprises a valve arrangement in which respective valves are associated with the extraction lines and a controller for selectively opening the valves.

3. The wind turbine power transmission system of claim 2, wherein the drain lines converge before the tank and at least one of the extraction lines is connected downstream from where the drain lines converge so as to be associated with a combined flow from the consumers.

4. The wind turbine power transmission system of claim 1, wherein the different consumers of the lubrication system include one or more main bearings supporting a main shaft, a gearbox driven by the main shaft, and a generator driven by an output of the gearbox.

5. The wind turbine power transmission system of claim 1, wherein the measurement device is connected to the output line downstream of the multiplexer and upstream of the tank.

6. A wind turbine power transmission system having different consumers of lubrication to be monitored via their lubricant, the power transmission system including a lubrication system, the lubrication system comprising:
 a tank;
 drain lines configured to receive lubricant from the different consumers, the drain lines being connected to the tank;
 extraction lines connected to the drain lines or the consumers;
 a multiplexer connected to the extraction lines, the multiplexer having an output line and being configured to selectively direct flow from the extraction lines to the output line;
 a measurement device connected to the output line, the measurement device being configured to measure a characteristic of the lubricant in the output line; and
 a pump connected to the output line, the pump being configured to draw lubricant through the multiplexer,
 wherein the multiplexer includes a valve arrangement in which respective valves are associated with the extraction lines and a controller for selectively opening the valves, and
 wherein the drain lines converge before the tank and one of the extraction lines is connected downstream from where the drain lines converge so as to direct a combined flow from all of the consumers connected to the multiplexer to the multiplexer.

7. The wind turbine power transmission system of claim 6, wherein the measurement device includes a particle counter configured to detect particles in the lubricant received from the multiplexer.

8. The wind turbine power transmission system of claim 7, further comprising a particle collector connected to the particle counter and configured to gather particles greater than a predetermined minimum sized detected by the particle counter.

9. The wind turbine power transmission system of claim 6, wherein the different consumers of the lubrication system include one or more main bearings supporting a main shaft, a gearbox driven by the main shaft, and a generator driven by an output of the gearbox.

* * * * *